US008696641B1

(12) United States Patent
Williams, III

(10) Patent No.: US 8,696,641 B1
(45) Date of Patent: Apr. 15, 2014

(54) MALE INCONTINENCE CONTAINMENT DEVICE

(76) Inventor: Archie B. Williams, III, New Smyrna Beach, FL (US)

(*) Notice: Subject to any disclaimer, the term of this patent is extended or adjusted under 35 U.S.C. 154(b) by 53 days.

(21) Appl. No.: 12/932,889

(22) Filed: Mar. 10, 2011

(51) Int. Cl.
*A61F 5/44* (2006.01)

(52) U.S. Cl.
USPC .......................................... 604/349; 604/351

(58) Field of Classification Search
USPC ........... 604/346–354, 544; 128/844, 885–886
See application file for complete search history.

(56) References Cited

U.S. PATENT DOCUMENTS

| | | | |
|---|---|---|---|
| 1,105,488 A | | 7/1914 | Clare |
| 2,586,674 A | | 2/1952 | Lönne |
| 2,699,781 A | | 1/1955 | Koch |
| 3,353,538 A | | 11/1967 | Carrigan |
| 3,511,241 A | | 5/1970 | Lee |
| 4,239,044 A | | 12/1980 | Pavlinch |
| 4,428,375 A | * | 1/1984 | Ellman ........................ 606/151 |
| 4,790,835 A | | 12/1988 | Elias |
| 5,078,707 A | * | 1/1992 | Peter Klug .................... 604/349 |
| 5,499,977 A | | 3/1996 | Marx |
| 5,662,631 A | | 9/1997 | Marx |
| 5,797,890 A | | 8/1998 | Goulter et al. |
| 6,430,755 B1 | | 8/2002 | Smith |
| 6,620,142 B1 | | 9/2003 | Flückiger |
| 7,152,603 B1 | * | 12/2006 | Crump et al. ............. 128/207.14 |
| 7,351,200 B2 | * | 4/2008 | Alferness ........................ 600/37 |
| D589,610 S | | 3/2009 | Dubose, Jr. |
| 7,780,642 B2 | | 8/2010 | Rasmussen et al. |
| 2003/0018321 A1 | * | 1/2003 | Rosenblum ................... 604/544 |
| 2005/0177119 A1 | * | 8/2005 | Tsai .............................. 604/332 |
| 2006/0004332 A1 | | 1/2006 | Marx |
| 2006/0229576 A1 | * | 10/2006 | Conway et al. ............... 604/349 |
| 2007/0038193 A1 | * | 2/2007 | Miskie .......................... 604/349 |
| 2008/0047854 A1 | * | 2/2008 | Golden et al. ............. 206/308.1 |

* cited by examiner

*Primary Examiner* — Oren Ginsberg
*Assistant Examiner* — Jennifer M Deichl
(74) *Attorney, Agent, or Firm* — Allen, Dyer, et al.

(57) ABSTRACT

A male incontinence containment device. A sleeve made of flexible mesh terminates at one end in a sleeve mouth, and at an opposite end in a sleeve floor. An absorptive pad is disposed inside the sleeve adjacent the sleeve floor. The sleeve mouth and sleeve are sized to admit a human penis. When urine from a penis inside the sleeve accumulates in the absorptive pad, gravity pulls the absorptive pad, and its sleeve end, downwards. This downwards motion causes the sleeve width to decrease and the sleeve to firmly grip the penis, thus preventing the incontinence containment device from slipping off the penis. A tear line is disclosed to for quick and easy removal. Alternate embodiments incorporating a removable end cap, and a hinged floor, respectively are disclosed permitting removal of a soiled absorptive pad and its replacement with a fresh absorptive pad.

13 Claims, 6 Drawing Sheets

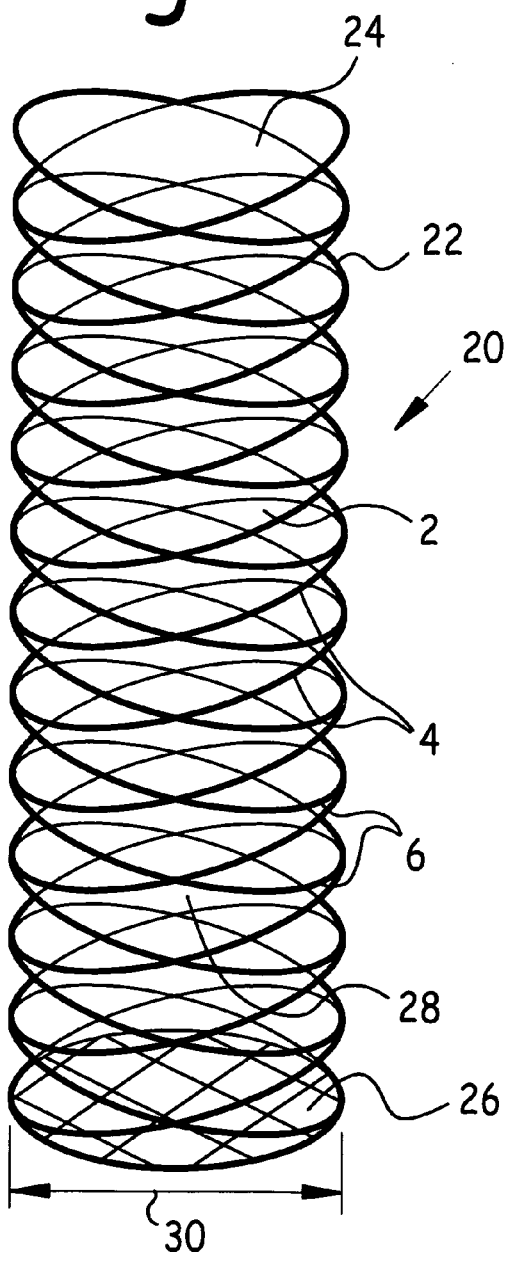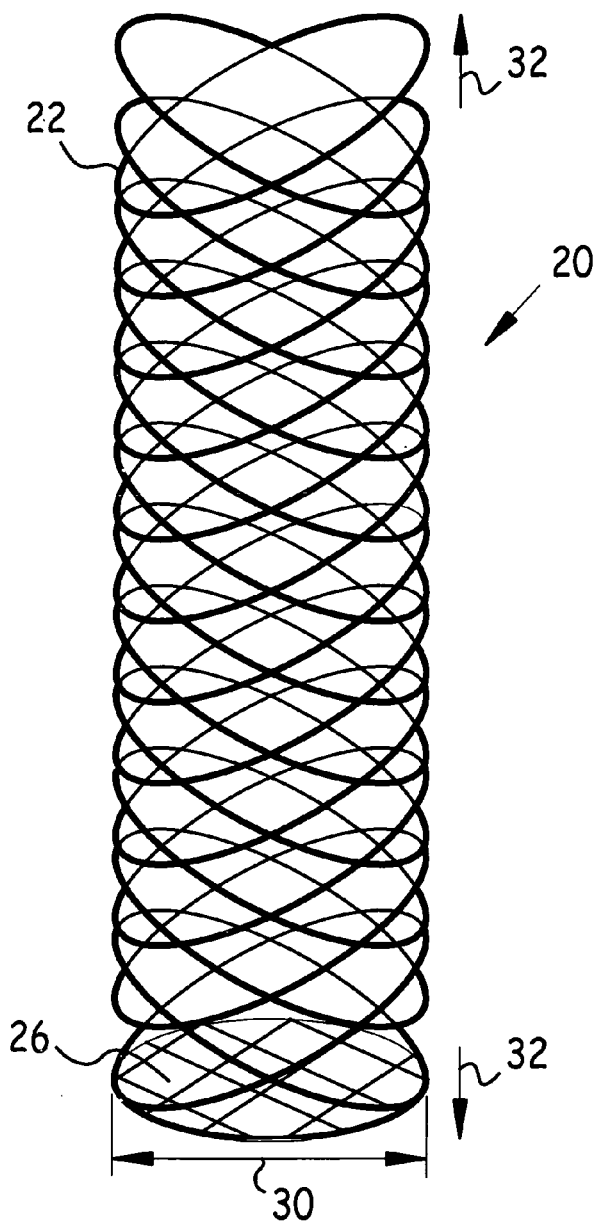

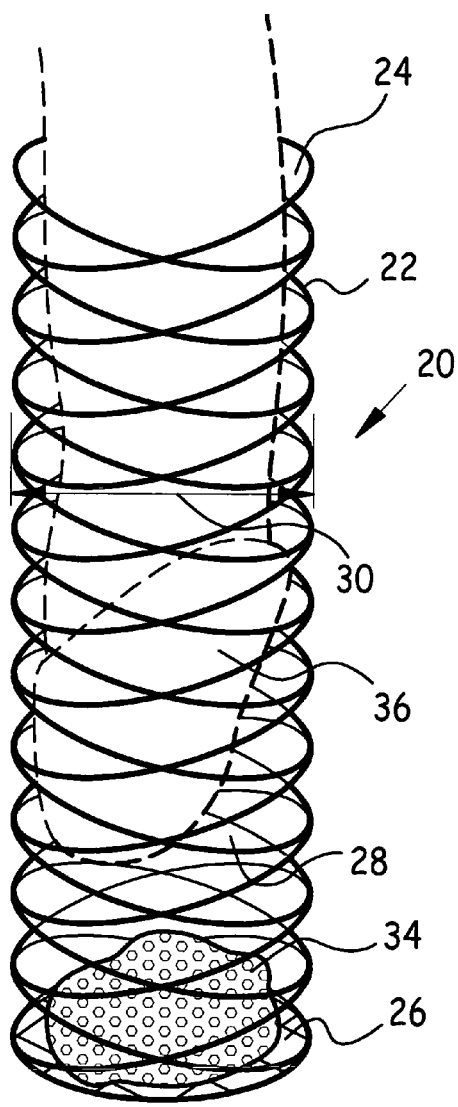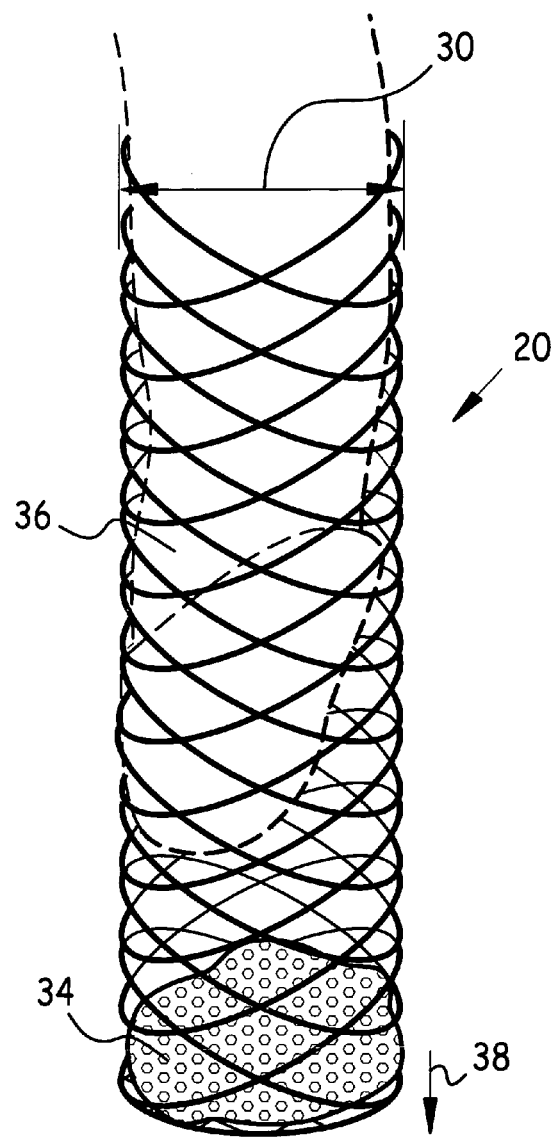

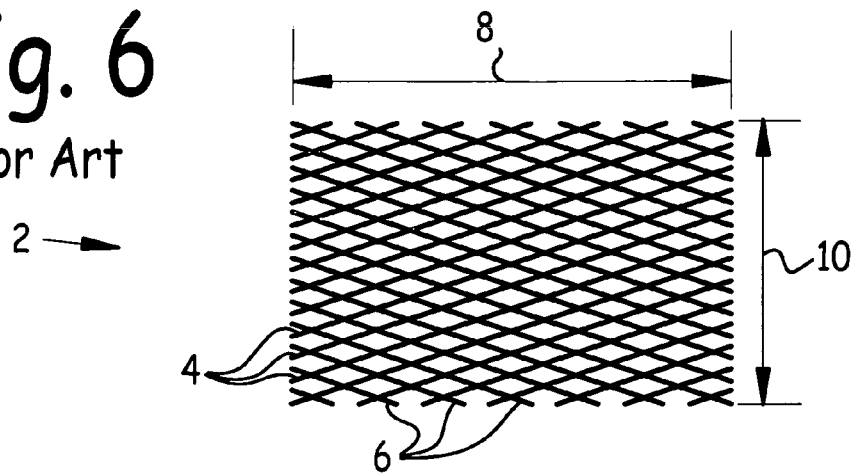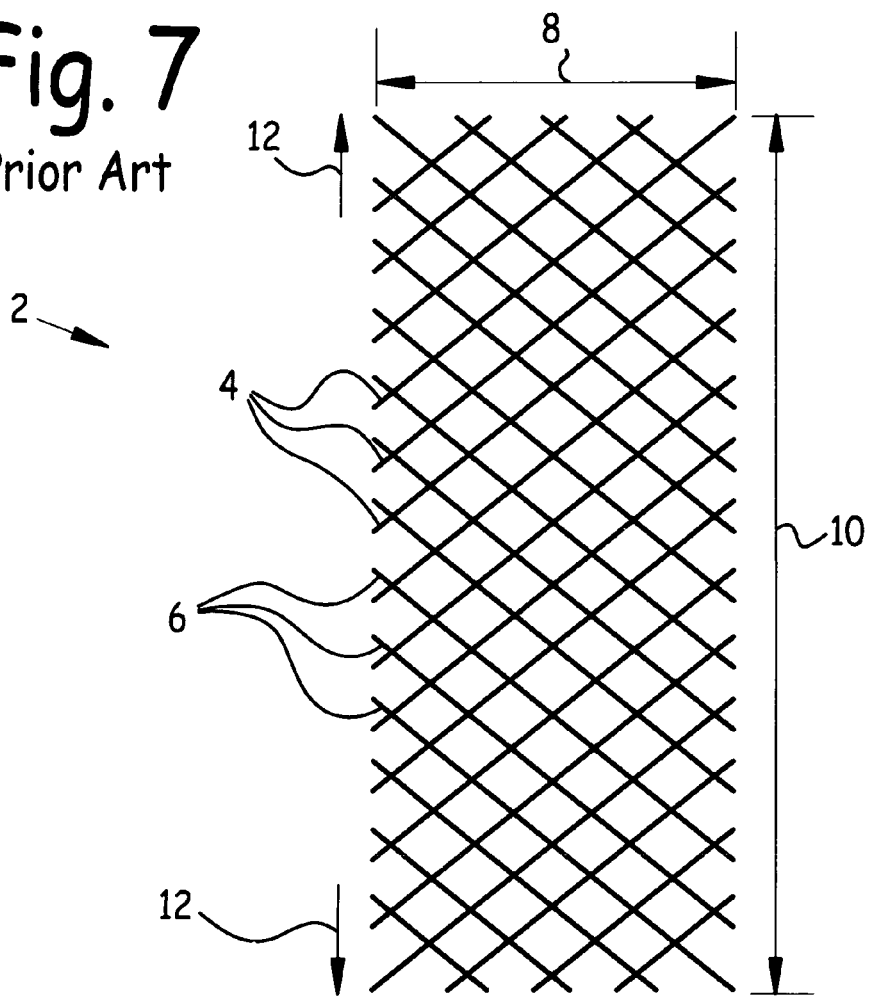

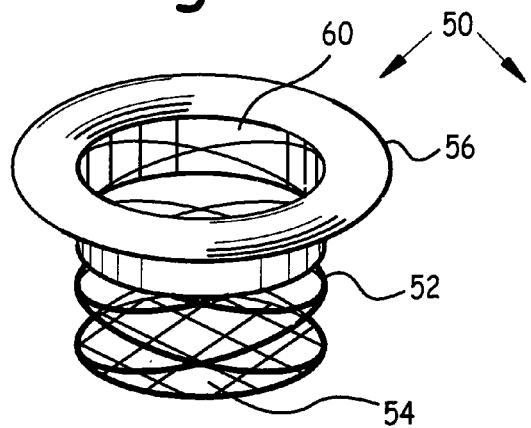
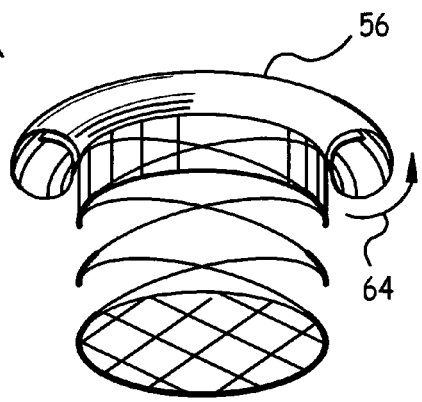
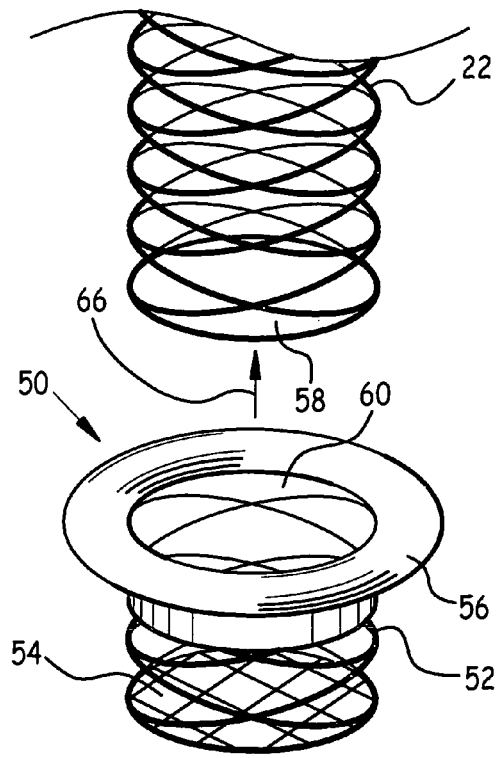
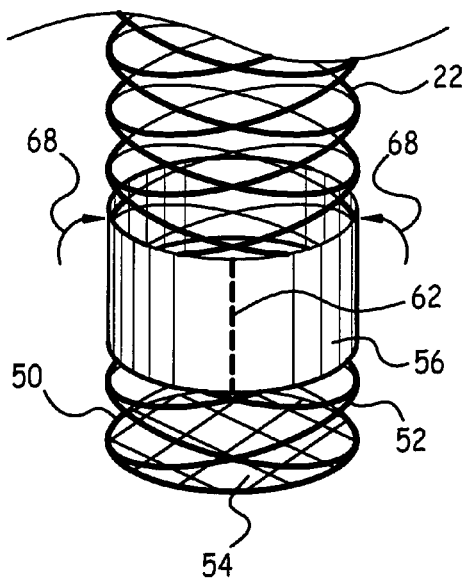

MALE INCONTINENCE CONTAINMENT DEVICE

BACKGROUND OF THE INVENTION

1. Field of the Invention

This invention relates to anti-incontinence devices, and in particular to a male incontinence containment device.

2. Background of the Invention

Urinary incontinence presents a major problem in human beings, afflicting some twenty-five million individuals in the United States alone. Of these, around eight million are male.

The problem can stem from a number of causes, including nervous system diseases such as Parkinson's disease, multiple sclerosis, and Alzheimer's disease. Bladder spasms causing incontinence can occur in the aftermath of strokes. Long-term diabetes can produce nerve damage, which in turn may affect control of the bladder. Head or spinal injury can short-circuit brain and nerve functions that control the urinary tract, and interrupt the neuro-signals required for proper control.

Prostate problems can overflow into the urinary tract area, and this syndrome affects significant numbers of men. Overflow incontinence occurs when the urethra is under pressure by some sort of obstruction. In this situation, the bladder fills to the point of overflow, and then dribbles throughout the day. Male overflow incontinence is almost always caused by an enlarged prostate gland which puts pressure on the urethra. Prostate enlargement can be caused by cancer, prostatitis, or simply by natural aging.

Urinary incontinence can also be caused by stress, such as surgery. Prostate surgery may involve removal of the prostate gland, and is called radical prostatectomy. When present, the prostate gland helps the urethral sphincter in its function by supporting the bladder neck. If the prostate is removed, it is no longer available to provide this assistance, and consequently temporary post-operation urinary incontinence is symptomatic in some ninety percent of men who have had a radical prostatectomy. Fifteen to twenty percent of these will continue to experience ongoing problems with urinary incontinence.

Accordingly, it is a pressing problem to provide some means of absorption for the urine which results from male urinary incontinence, be it temporary or chronic.

Most urinary absorptive pads are designed for the female anatomy, which is much more amenable to this type of device. In men, however, urine ordinarily emerges from the tip of the penis, which tends to move around during the course of the day (and during the course of the night too, for that matter), thus presenting a "moving target". Complicating the matter is that urinary tract infection is rendered more probable if the tip of the penis is in contact with urine, or with an absorptive pad which is wet with urine.

Thus it would be desirable to provide a means of holding an absorptive pad in a position to catch urine when it emerges from the penis tip, yet at the same time also hold the absorptive pad out of contact with the penis tip in order to help avoid urethral tract infection. In addition, it would be advantageous to provide means to quickly and easily remove the device from the penis after use.

In addition, it would be desirable to provide means to quickly and easily replace a soiled absorptive pad with a fresh one, without removing the rest of the male incontinence containment from a penis from which it depends.

Existing Designs

A number of patents have issued for male urinary anti-incontinence devices, but these suffer from a number of problems. U.S. Pat. No. 7,727,206 was granted to Gorres for an internal catheter. Insertion and removal of this device required specialized knowledge, and there was certain risk associated with its use. The patient generally could not self-administer this device.

Several patents for external catheters have been issued: U.S. Pat. No. 6,620,142 to Flückiger; U.S. Pat. No. 7,780,642 to Rasmussen et al.; U.S. Pat. No. 5,797,890 to Goulter et al.; U.S. Pat. No. 5,662,631 to Marx; U.S. Pat. No. 5,499,977 to Marx; U.S. Pat. No. 4,790,835 to Elias; U.S. Pat. No. 4,239,044 to Pavlinch; U.S. Pat. No. 3,511,241 Lee; U.S. Pat. No. 3,353,538 to Carrigan; U.S. Pat. No. 2,699,781 to Koch; U.S. Pat. No. 1,105,488 to Clare; and U.S. Pat. No. D589,610 to Dubose, Jr. In addition, currently pending is U.S. Pat. App. Pub. No. 2006/0004332 filed by Marx. The devices taught by these documents were complex and therefore expensive; some were made of rigid components and may therefore have been uncomfortable, and many taught no absorptive pad to absorb unwanted urine. Where an absorptive pad was disclosed, it frequently allowed the urine-soaked absorptive pad to remain in contact with the tip of the penis where the urethra exits the penis, thus increasing the risk of urinary tract infection. In addition, the retention means taught by these devices frequently relied on circumferential straps which applied pressure to the penis, which could be uncomfortable and unyielding.

U.S. Pat. No. 2,586,674 was granted to Lönne for a prophylactic device. While the Lönne prophylactic taught a criss-cross pattern of external diagonally-disposed ribs encircling a portion of its outer surface, these were disclosed as being zones of less tension for sperm collection, and did not function to keep the prophylactic retained in place on the user's penis. No absorptive pad was taught.

U.S. Pat. No. 6,430,755 was granted to Smith for a bodily waste collector which incorporated a plastic film material tear line to convert the device from male to female use and to collect feces. No tear line was disclosed to facilitate removal of the Smith device from the wearer's penis. In addition, the Smith device allowed the urine-soaked absorptive pad to remain in contact with the tip of the penis where the urethra exits the penis, thus increasing the risk of urinary tract infection.

SUMMARY OF THE INVENTION

Accordingly, it is an object of the present invention to provide a male incontinence containment device which automatically tightens around a penis it encases when an absorptive pad inside its distal end becomes wet. Design features allowing this object to be accomplished include a mesh sleeve sized to slidably admit a male penis, a sleeve mouth at a sleeve proximal end, a sleeve floor at a sleeve distal end, and an absorptive pad disposed inside the sleeve distal end. Advantages associated with the accomplishment of this object include reduced leakage and increased wearer comfort.

It is another object of the present invention to provide a male incontinence containment device which prevents leakage due to male incontinence. Design features allowing this object to be accomplished include a mesh sleeve sized to slidably admit a male penis, a sleeve mouth at a sleeve proximal end, a sleeve floor at a sleeve distal end, and an absorptive pad disposed inside the sleeve distal end. Advantages associated with the accomplishment of this object include reduced leakage and increased wearer comfort.

It is still another object of this invention to provide a male incontinence containment device which is easy to remove after use. Design features enabling the accomplishment of this object include an upsloping strand reduced cross-sectional area in each upsloping strand, and a downsloping strand reduced cross-sectional area in each downsloping strand, the upsloping strand reduced cross-sectional areas and downsloping strand reduced cross-sectional areas being substantially co-linear. Advantages associated with the realization of this object include ease of use to the wearer, and better hygiene due to less handling of the soiled containment device.

It is another object of the present invention to provide a male incontinence containment device which prevents its absorptive pad from coming into direct contact with the tip of the penis when wet. Design features allowing this object to be accomplished include a mesh sleeve sized to slidably admit a male penis, a sleeve mouth at a sleeve proximal end, a sleeve floor at a sleeve distal end, and an absorptive pad disposed inside the sleeve distal end, which when wet tends to pull the distal sleeve down, away from the penis tip. Advantages associated with the accomplishment of this object reduced likelihood of urinary tract infection, and increased wearer comfort.

It is still another object of the present invention to provide a male incontinence containment device which provides means to quickly and easily replace a soiled absorptive pad with a fresh one, without removing the rest of the male incontinence containment from a penis from which it depends. Design features allowing this object to be accomplished include an end cap which is removable from, and re-attachable to, the distal end of a sleeve. Advantages associated with the accomplishment of this object increased wearer comfort and convenience of use, and reduced cost.

It is still another object of the present invention to provide a male incontinence containment device which provides means to quickly and easily replace a soiled absorptive pad with a fresh one, without removing the rest of the male incontinence containment from a penis from which it depends. Design features allowing this object to be accomplished include a closable hinged floor pivotally attached to the distal end of a sleeve. Advantages associated with the accomplishment of this object increased wearer comfort and convenience of use, and reduced cost.

It is yet another object of this invention to provide a male incontinence containment device which is inexpensive to manufacture. Design features allowing this object to be achieved include the use of components made of readily available materials. Benefits associated with reaching this objective include reduced cost, and hence increased availability.

BRIEF DESCRIPTION OF THE DRAWINGS

The invention, together with the other objects, features, aspects and advantages thereof will be more clearly understood from the following in conjunction with the accompanying drawings.

Six sheets of drawings are provided. Sheet one contains FIGS. 1 and 2. Sheet two contains FIGS. 3 and 4. Sheet three contains FIG. 5. Sheet four contains FIGS. 6 and 7. Sheet 5 contains FIGS. 8, 9, 10, and 11. Sheet six contains FIGS. 12 and 13.

FIG. 1 is a side isometric view of a male incontinence containment device in the resting configuration.

FIG. 2 is a side isometric view of a male incontinence containment device in an extended configuration.

FIG. 3 is a male incontinence containment device emplaced on a penis in the resting configuration.

FIG. 4 is a side isometric view of a male incontinence containment device emplaced on a penis in an extended configuration, as urged by the weight of the moistened absorptive pad.

FIG. 6 is a plan view of a section of prior art mesh made up of upsloping strands and downsloping strands, in the resting configuration.

FIG. 7 is a plan view of a section of prior art mesh made up of upsloping strands and downsloping strands, in an extended configuration.

FIGS. 8-11 are side isometric views of an alternate embodiment male incontinence containment device incorporating a sleeve distal aperture and a removable end cap.

FIG. 8 is a side isometric view of an end cap, with its end cap elastic sleeve rolled up.

FIG. 9 is a side isometric cross-sectional view of an end cap, with its end cap elastic sleeve rolled up.

FIG. 10 is a side isometric cross-sectional view of an end cap about to be emplaced on the distal end of a sleeve, over the sleeve distal aperture.

FIG. 11 is a side isometric view of an end cap installed on the distal end of a sleeve, with its end cap elastic sleeve unrolled over the sleeve distal end.

DETAILED DESCRIPTION OF THE PREFERRED EMBODIMENT

Figure 5:
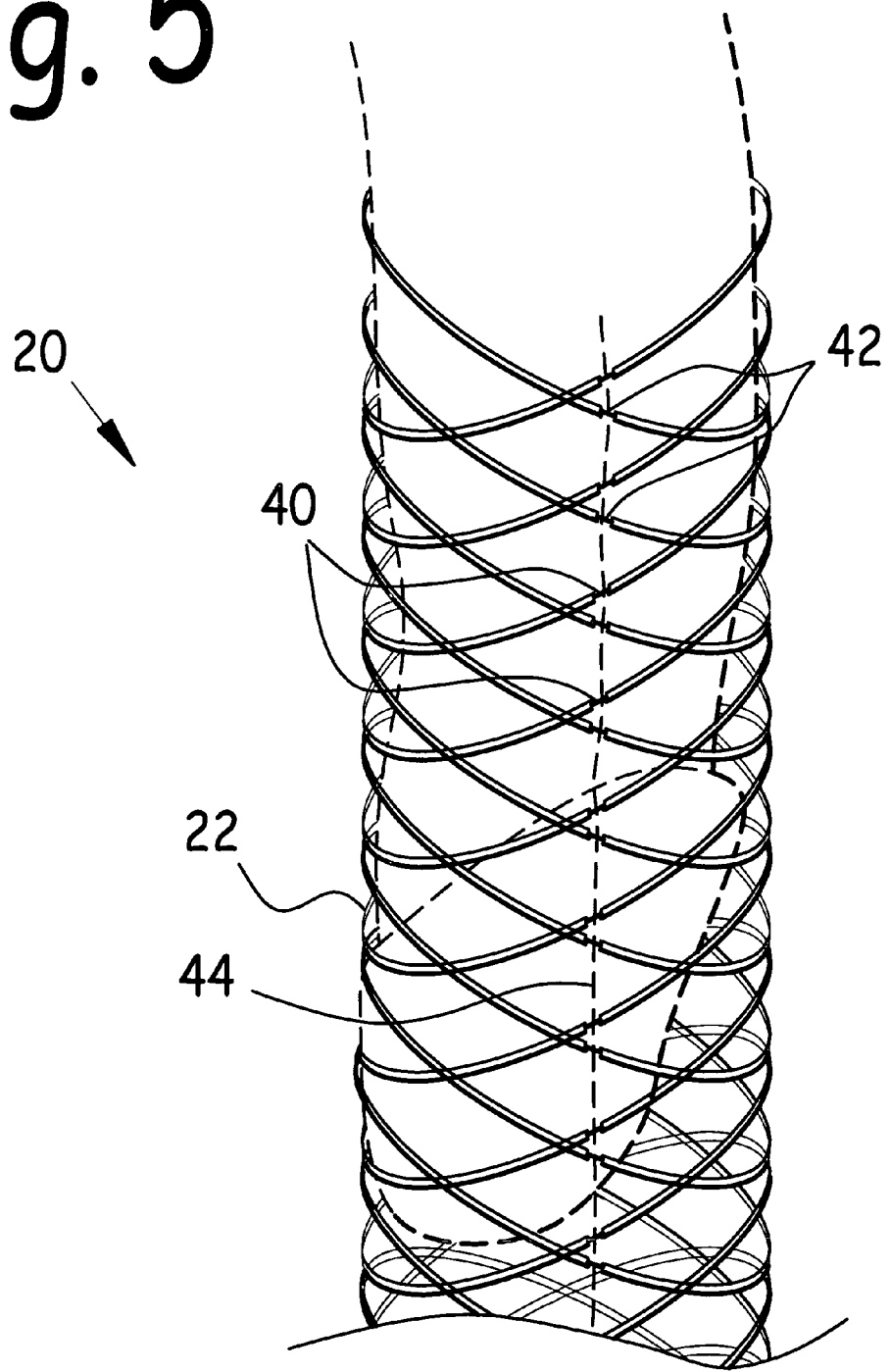
FIG. 5 is a close-up side isometric view of a male incontinence containment device showing its tear line made up of upsloping strand reduced cross-sectional areas and downsloping strand reduced cross-sectional areas.

FIG. 6 is a plan view of a section of prior art mesh 2 made up of upsloping strands 4 and downsloping strands 6, in the resting configuration. FIG. 7 is a plan view of a section of prior art mesh 2 made up of upsloping strands 4 and downsloping strands 6, in an extended configuration.

As may be observed in FIGS. 6 and 7, mesh 2 is comprised of a plurality of substantially parallel upsloping strands 4 attached to a plurality of substantially parallel downsloping strands 6, at intersections of upsloping strands 4 with downsloping strands 6.

Mesh 2 may be manufactured of flexible material such as nylon, plastic, synthetic, or other appropriate material, and is commercially available. The flexible nature of the material from which mesh 2 is manufactured enables it to deform as is depicted in FIG. 7.

FIG. 6 depicts mesh 2 in the resting, or non-stressed position, in which it has mesh width 8 and mesh height 10. Starting out from the rest position shown in FIG. 6, mesh 2 may be extended by pulling on its upper and lower edges as indicated by arrows 12 in FIG. 7. The flexible nature of its material allows mesh 2 to extend up and down, such that its extended mesh height 10 as shown in FIG. 7 is greater than the mesh height 10 indicated in FIG. 6. Due to the crisscrossed positioning of upsloping strands 4 and downsloping strands 6, extension of mesh 2 as shown in FIG. 7 causes mesh width 8 to decrease from the resting configuration mesh width 8 shown in FIG. 6.

Thus, pulling mesh 2 into the extended position depicted in FIG. 7 causes mesh width 8 to decrease relative to the resting mesh width 8 shown in FIG. 6.

This principle of mesh dynamics is used in Chinese Handcuffs, which comprises a cylinder made of mesh material similar to that illustrated in FIGS. 6 and 7. The Chinese Handcuffs cylinder is sized to slidably admit a human finger through each end. When the fingers are sought to be extracted, friction between the fingers and the mesh cylinder pulls its ends apart, thus extending the cylinder and reducing its circumference, trapping the fingers inside.

This principle of finger entrapment is used in the instant invention, except the instant invention comprises mesh sleeve 22 sized to admit a human penis, and the penis is entrapped when sleeve 22 is extended, e.g. by the weight of moist absorptive pad 34 at its distal end. The entrapment of the penis by extended mesh sleeve 22 serves to prevent the instant incontinence containment device from slipping off the penis.

The instant incontinence containment device 20 may be removed from a penis which it grips in the same way that fingers are liberated from Chinese Handcuffs: by reducing the length of sleeve 22 sufficiently to allow sleeve width 30 to increase to the extent necessary to slip the penis out of incontinence containment device 20.

In the alternative, the instant invention also teaches a lengthwise tear line 44 made up of upsloping strand reduced cross-sectional areas 40 and downsloping strand reduced cross-sectional areas 42, as depicted in FIG. 5. In this embodiment, incontinence containment device 20 may be quickly and easily removed from penis 36 simply by tearing sleeve 22 along tear line 44, and then removing incontinence containment device 20 from penis 36.

FIG. 1 is a side isometric view of male incontinence containment device 2 in the resting configuration. FIG. 2 is a side isometric view of incontinence containment device 20 in an extended configuration.

Incontinence containment device 20 comprises sleeve 22 having sleeve interior 28 sized to slidably admit penis 36. Sleeve 22 terminates at sleeve mouth 24 at its proximal end, and at sleeve floor 26 at its distal end. Sleeve mouth 24 is also sized to slidably admit penis 36.

Sleeve 22 is made of mesh 2 comprising a plurality of substantially parallel upsloping strands 4 attached to a plurality of substantially parallel downsloping strands 6, at intersections of upsloping strands 4 with downsloping strands 6.

The flexible nature of the material from which mesh 2 is manufactured enables incontinence containment device 20 to deform into the extended configuration depicted in FIG. 2, when its ends are pulled apart as indicated by arrows 32.

The flexible nature the material of which mesh 2 is made allows sleeve 22 to extend up and down, such that its extended height as shown in FIG. 2 is greater than its resting height as indicated in FIG. 1. Due to the crisscrossed positioning of upsloping strands 4 and downsloping strands 6, extension of sleeve 22 as shown in FIG. 2 causes sleeve width 30 to decrease from the resting configuration mesh width shown in FIG. 1.

Sleeve floor 26 may also be manufactured of mesh 22.

FIG. 3 is a side isometric view of a male incontinence containment device 20 emplaced on penis 36 in the resting configuration. FIG. 4 is a side isometric view of incontinence containment device 20 emplaced on penis 36 in an extended configuration, as urged by the weight of moistened absorptive pad 34.

As may be observed in FIGS. 3 and 4, incontinence containment device 20 further comprises absorptive pad 34 disposed within sleeve 22 adjacent sleeve floor 26. When the wearer of incontinence containment device 20 experiences incontinence, urine emerges from penis 36 and dribbles onto absorptive pad 34.

As absorptive pad 36 accumulates urine its weight pulls the distal end of sleeve 22 downwards under the influence of gravity, as is indicated by arrow 38 in FIG. 4. As explained above, this increase in length of sleeve 22 causes its sleeve width 30 to decrease, and causes sleeve 22 to grip penis 36 sufficiently to prevent incontinence containment device 20 from slipping off of penis 36. Thus, the weight of moistened absorptive pad 34 causes sleeve 22 to securely grip penis 36, thus holding incontinence containment device 20 in position until it is desired to remove incontinence containment device 20 from penis 36.

FIG. 5 is a close-up side isometric view of male incontinence containment device 20 incorporating a lengthwise, substantially co-linear tear line 44 made up of upsloping strand reduced cross-sectional areas 40 and downsloping strand reduced cross-sectional areas 42. Tear line 44 is depicted by a dashed line in FIG. 5. In this embodiment, incontinence containment device 20 may be quickly and easily removed from penis 36 simply by tearing sleeve 22 along tear line 44, and then removing incontinence containment device 20 from penis 36.

During the course of use, absorptive pad 34 may become imbued with urine, and need to be replaced. Short of replacing the entire incontinence containment device 20, it would be desirable to replace only absorptive pad 34, while leaving sleeve 20 in place. The embodiments of FIGS. 8-11, and 13 and 14, permit absorptive pad 34 to be quickly and easily replaced while leaving sleeve 20 in place.

FIGS. 8-11 are side isometric views of an alternate embodiment male incontinence containment device 20 incorporating sleeve distal aperture 58 at an end of sleeve 20 opposite sleeve mouth 24, and removable end cap 50. In the embodiment illustrated in FIGS. 8-11, floor 26 has been omitted from the construction of the distal end of sleeve 22, leaving sleeve distal aperture 58 at the distal end of sleeve 22. Thus, in this embodiment, sleeve interior 28 communicates with an exterior of sleeve interior 28 through sleeve mouth 24 at its proximal end and sleeve distal aperture 58 at its distal end.

In use, incontinence containment device 20 with end cap 50 containing absorptive pad 34 it its distal end would be emplaced on penis 20 as previously described. After absorptive pad 34 becomes imbued with urine and requires replacement with a fresh absorptive pad 34, end cap 50 containing the soiled absorptive pad 34 is removed from sleeve 22, and a fresh end cap 50 containing a fresh absorptive pad 34 is emplaced on the distal end of sleeve 22.

FIG. 8 is a side isometric view of end cap 50, with its end cap elastic sleeve 56 rolled up. FIG. 9 is a side isometric cross-sectional view of end cap 50, with its end cap elastic sleeve 56 rolled up. As may be observed in these figures, end cap 50 comprises end cap sleeve 52, end cap mouth 60 at one end of end cap sleeve 52, and end cap floor 54 at an opposite end of end cap sleeve 52 from end cap mouth 60.

End cap sleeve 52 is of substantially the same diameter as sleeve 22, and may be made of similar mesh material as sleeve 22, or any other appropriate material.

End cap elastic sleeve 56 is attached circumferentially around end cap sleeve 52 at the end of end cap sleeve 52 where end cap mouth 60 is disposed. The diameter of end cap elastic sleeve 56 is substantially the same or slightly less than the diameter of sleeve 22, which permits end cap elastic sleeve 56 to frictionally grip sleeve 22 when end cap elastic sleeve 56 is unrolled over sleeve 22 as depicted in FIGS. 10 and 11.

Initially, end cap sleeve 50 is provided with it end cap elastic sleeve rolled up (as depicted in FIGS. 8 and 9), ready to be unrolled over sleeve 22 as depicted in FIGS. 10 and 11, in similar fashion to the way the proximal end of a prophylactic or condom is initially provided out of the package in a rolled-up configuration, ready to be unrolled over a penis. End cap 50 is attached to the distal end of sleeve 22 by unrolling end cap elastic sleeve 56 over sleeve 22 distal end, like a prophylactic or condom is emplaced on a penis by unrolling its proximal end over the penis.

FIG. 10 is a side isometric cross-sectional view of end cap 50 about to be emplaced on the distal end of a sleeve 22, capping the sleeve distal aperture 58. FIG. 11 is a side isometric view of end cap 50 installed on the distal end of sleeve 22, with its end cap elastic sleeve 56 unrolled over the sleeve distal end.

As may be observed in these figures, once an end cap 50 containing a soiled absorptive pad 34 has been removed from the distal end of sleeve 22, a new end cap 50 containing a fresh absorptive pad 34 may be quickly and easily emplaced on the distal end of sleeve 22, by unrolling end cap elastic sleeve 56 over the distal end of sleeve 22, as indicated by arrow 64 in FIG. 9.

First, end cap 50 containing a fresh absorptive pad 34 and its end cap elastic sleeve in a rolled-up configuration is positioned so that its end cap mouth 60 is adjacent sleeve distal aperture 58 and substantially co-extends with sleeve distal aperture 58, as indicated by arrow 66 in FIG. 10.

Second, end cap elastic sleeve 56 is unrolled over the distal end of sleeve 22, as indicated by arrows 68 in FIG. 11. Because the diameter of end cap elastic sleeve 56 is substantially the same as, or slightly less than, the diameter of the distal end of sleeve 22, end cap elastic sleeve 56 when unrolled frictionally grips the distal end of sleeve 22, thus holding end cap 50 firmly in place on the distal end of sleeve 22.

In interest of clarity, absorptive pad 34 has not been depicted in FIGS. 8-11, although it is intended to be understood that end cap 50 contains a fresh absorptive pad 34 throughout the installation steps described above.

End cap elastic sleeve 56 may incorporate an end cap elastic sleeve tear line 62, as depicted in FIG. 11. End cap elastic sleeve tear line 62 is a series of substantially co-linear apertures in end cap elastic sleeve 56, which facilitate the tearing of end cap elastic sleeve 56 along end cap elastic sleeve tear line 62 when it is sought to remove end cap 50 from sleeve 22, e.g. for absorptive pad 34 replacement. In the preferred embodiment, end cap elastic sleeve tear line 62 was disposed in end cap elastic sleeve 56 substantially parallel to a centerline of end cap 50. Thus, end cap 50 may be quickly and easily removed from sleeve 22 by tearing end cap elastic sleeve 56 along end cap elastic sleeve tear line 62, and then simply removing end cap 50 from sleeve 22 opposite the sense of arrow 66 in FIG. 10.

Thus, in the embodiment depicted in FIGS. 8-11, incontinence containment device 20 may be supplied initially with end cap 50 containing fresh absorptive pad 34 attached to the distal end of sleeve 22. Incontinence containment device 20 is emplaced on penis 36 as described previously. When absorptive pad 34 becomes soiled, it can be quickly and easily replaced by tearing along end cap elastic sleeve tear line 62 and removing end cap 50 from sleeve 22, and replacing it with a fresh end cap 60 containing a fresh absorptive pad 34, installed by unrolling end cap elastic sleeve 56 over the distal end of sleeve 22. Over a period of time, multiple fresh end caps 50 with fresh absorptive pads 34 may be emplaced serially as described above, as necessary.

Figure 12:
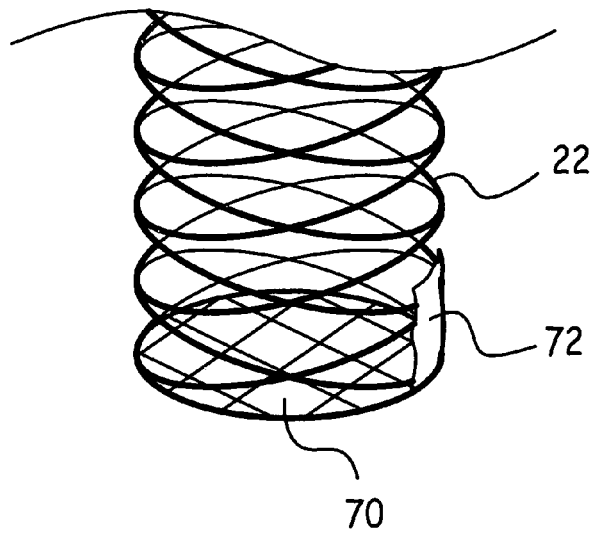
FIG. 12 is a side isometric view of an alternate embodiment male incontinence containment device incorporating a hinged floor pivotally attached to the distal end of a sleeve, adjacent a sleeve distal aperture, with the hinged floor held in the closed position by a hinged floor tab.
Figure 13:
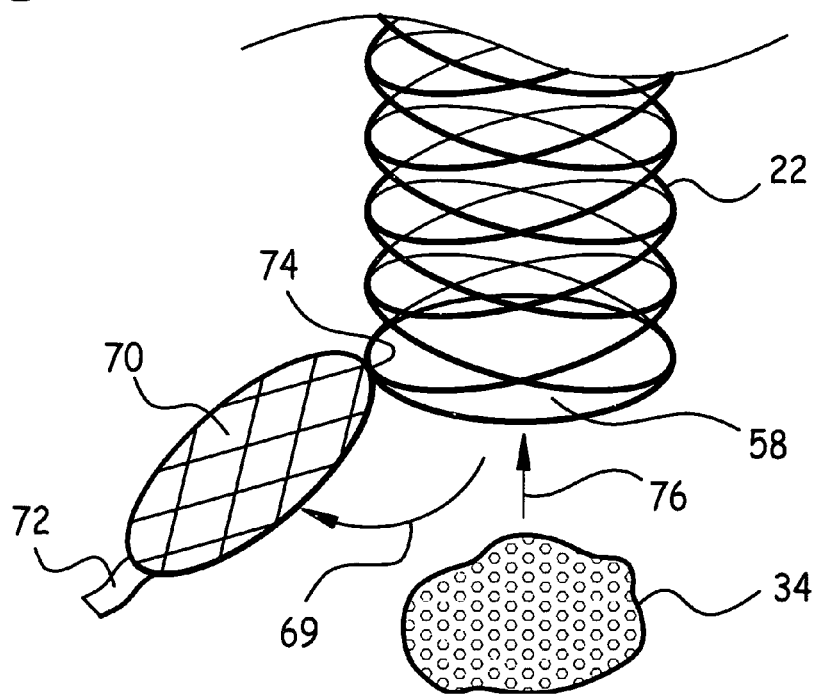
FIG. 13 is a side isometric view of an alternate embodiment male incontinence containment device incorporating a hinged floor pivotally attached to the distal end of a sleeve, adjacent a sleeve distal aperture, with the hinged floor in the open position.

FIGS. 12 and 13 depict another alternate embodiment of the instant invention which permits quick and easy replacement of a soiled absorptive pad 34 with a fresh absorptive pad 34. As in the previous alternate embodiment described above, sleeve floor 26 has been omitted from the construction of the distal end of sleeve 22, leaving sleeve distal aperture 58 at its distal end. Thus, in this embodiment, sleeve interior 28 communicates with an exterior of sleeve interior 28 through sleeve mouth 24 at its proximal end and sleeve distal aperture 58 at its distal end.

FIG. 12 is a side isometric view of an alternate embodiment male incontinence containment device 20 incorporating hinged floor 70 pivotally attached to the distal end of sleeve 22, adjacent sleeve distal aperture 58, with hinged floor 70 held in the closed position by hinged floor tab 72. FIG. 13 is a side isometric view of an alternate embodiment male incontinence containment device 20 incorporating hinged floor 70 pivotally attached to the distal end of sleeve 22, adjacent sleeve distal aperture 58, with hinged floor 70 in the open position.

Hinged floor 70 is attached to the distal end of sleeve 22 at hinged floor pivot point 74. Hinged floor tab 72 is attached to hinged floor 70, and serves to maintain hinged floor 70 in the closed position depicted in FIG. 12. To that end, hinged floor tab 72 may have an adhesive coating or hook-and-look material attached, or other appropriate closure means, in order to removably and re-attachably adhere to sleeve 22 to maintain hinged floor 70 in the closed position depicted in FIG. 12. If hinged floor tab 72 incorporates hook-and-look material, then mating hook-and-loop material would be attached to sleeve 22.

When it is desired to remove a soiled absorptive pad 34 from sleeve interior 28 and replace it with a fresh one, hinged floor tab 72 detached from sleeve 22 and hinged floor 70 is opened as indicated by arrow 69 in FIG. 13. The soiled absorptive pad 34 is removed opposite the sense of arrow 76 in FIG. 13, and then a fresh absorptive pad 34 inserted as indicated by arrow 76 in FIG. 13. Finally, hinged floor 70 is closed opposite the sense of arrow 69 in FIG. 13, and hinged floor tab 72 re-attached to sleeve 22, thus securely holding hinged floor 70 in the closed position and the fresh absorptive pad 34 within sleeve interior 28, ready for use.

In the preferred embodiment, sleeve 22, end cap sleeve 52, sleeve floor 26, and hinged floor 70 were made of commercially available flexible mesh material of nylon, plastic, synthetic, or any other appropriate material. Absorptive pad 34 was made of cotton, diaper material, multi-layer absorptive material, or any other appropriate material capable of absorbing and holding moisture. End cap elastic sleeve 56 was made of elastic material such as thin rubber, latex, synthetic, or other appropriate material. Hinged floor tab 72 was made of flexible material such as fabric, rubber, synthetic, or other appropriate material, and had a closure means such as re-usable adhesive or hook-and-loop material attached.

While a preferred embodiment of the invention has been illustrated herein, it is to be understood that changes and variations may be made by those skilled in the art without departing from the spirit of the appending claims.

DRAWING ITEM INDEX 2 mesh
4 upsloping strand
6 downsloping strand 8 mesh width
10 mesh height
12 arrow
20 incontinence containment device
22 sleeve
24 sleeve mouth
26 sleeve floor
28 sleeve interior
30 sleeve width
32 arrow
34 absorptive pad
36 penis
38 arrow
40 upsloping strand reduced cross-sectional area
42 downsloping strand reduced cross-sectional area
44 tear line
50 end cap
52 end cap sleeve
54 end cap floor
56 end cap elastic sleeve
58 sleeve distal aperture
60 end cap mouth
62 end cap elastic sleeve tear line
64 arrow
66 arrow
68 arrow
69 arrow
70 hinged floor
72 hinged floor tab
74 hinged floor pivot point
76 arrow

I claim:

1. An incontinence containment device comprising a sleeve terminating in a sleeve mouth at one end, and at a sleeve floor in an opposite end, said sleeve being made of mesh comprised of a plurality of substantially parallel upsloping strands attached to a plurality of substantially parallel downsloping strands at intersections of said upsloping strands with said downsloping strands; wherein:
  said sleeve mouth and said sleeve are sized to slidably admit a male penis;
  a tear line in said sleeve comprises a plurality of upsloping strand reduced cross-sectional areas and a plurality of downsloping strand reduced cross-sectional areas; and
  said upsloping strand reduced cross-sectional areas and said downsloping strand reduced cross-sectional areas are disposed lengthwise along said sleeve, and are substantially co-linear.

2. The incontinence containment device of claim 1 wherein said mesh is made of flexible material whereby said sleeve may be pulled into an extended position, thereby reducing a width of said sleeve.

3. The incontinence containment device of claim 2 further comprising an absorptive pad disposed within said sleeve adjacent said sleeve floor.

4. An incontinence containment device comprising a sleeve terminating in a sleeve mouth at one end, and at a sleeve floor in an opposite end, said sleeve being made of flexible mesh comprised of a plurality of substantially parallel upsloping strands attached to a plurality of substantially parallel downsloping strands at intersections of said upsloping strands with said downsloping strands; wherein:
  a tear line in said sleeve comprises a plurality of upsloping strand reduced cross-sectional areas and a plurality of downsloping strand reduced cross-sectional areas; and
  said upsloping strand reduced cross-sectional areas and said downsloping strand reduced cross-sectional areas are disposed lengthwise along said sleeve, and are substantially co-linear.

5. The incontinence containment device of claim 4 further comprising an absorptive pad disposed within said sleeve adjacent said sleeve floor.

6. The incontinence containment device of claim 5 wherein said sleeve mouth and said sleeve are sized to slidably admit a male penis.

7. An incontinence containment device comprising a sleeve comprising a sleeve interior, a sleeve proximal end at one extreme of said sleeve, and a sleeve distal end at an extreme of said sleeve opposite said sleeve proximal end; a sleeve mouth at said sleeve proximal end, said sleeve communicating with an exterior of said sleeve through said sleeve mouth; a sleeve distal aperture at said sleeve distal end; a hinged floor pivotally attached to said sleeve distal end at a hinged floor pivot point; and means to openably hold said hinged floor closed, wherein said sleeve is made of mesh comprised of a plurality of substantially parallel upsloping strands attached to a plurality of substantially downsloping strands at intersections of said upsloping strands with said downsloping strands.

8. The incontinence containment device of claim 7 wherein said mesh is made of flexible material whereby said sleeve may be pulled into an extended position, thereby reducing a width of said sleeve sufficiently to allow said sleeve to grip a penis within said sleeve.

9. The incontinence containment device of claim 8 further comprising an absorptive pad disposed within said sleeve adjacent said hinged floor.

10. The incontinence containment device of claim 9 wherein said sleeve mouth and said sleeve are sized to slidably admit a male penis.

11. The incontinence containment device of claim 9 wherein said means to hold said hinged floor closed comprises a hinged floor tab attached to said hinged floor, and means to removably attach said hinged floor tab to said sleeve.

12. The incontinence containment device of claim 11 wherein said means to removably attach said hinged floor tab to said sleeve comprises adhesive on said hinged floor tab.

13. The incontinence containment device of claim 11 wherein said means to removably attach said hinged floor tab to said sleeve comprises hook-and-loop material on said hinged floor tab, and mating hook-and-loop material on said sleeve.

* * * * *